United States Patent
Momma et al.

[11] Patent Number: 6,160,240
[45] Date of Patent: Dec. 12, 2000

[54] METHOD OF PRODUCING MICROSTRUCTURAL MEDICAL IMPLANTS

[75] Inventors: Carslen Momma; Siefan Nolte, both of Hannover; Ferdinand von Alvensleben, Wennigsen; Armin Bolz, Buckenhof, all of Germany

[73] Assignee: Biotronik Mess-und Therapiegeräte GmbH & Co Ingenieurbüro Berlin, Berlin, Germany

[21] Appl. No.: 09/172,134

[22] Filed: Oct. 14, 1998

[30] Foreign Application Priority Data

Oct. 14, 1997 [DE] Germany .................... 197 45 294

[51] Int. Cl.[7] .................................................. B23K 26/00
[52] U.S. Cl. ........................... 219/121.85; 219/121.6; 219/121.68; 219/121.73
[58] Field of Search ................. 219/121.85, 121.6, 219/121.61, 121.67, 121.68, 121.73, 121.82

[56] References Cited

U.S. PATENT DOCUMENTS

| | | | |
|---|---|---|---|
| 5,041,109 | 8/1991 | Abela | 606/15 |
| 5,108,755 | 4/1992 | Daniels et al. | 424/426 |
| 5,206,341 | 4/1993 | Ibay et al. | 528/361 |
| 5,437,900 | 8/1995 | Kuzowski | 428/36.1 |
| 5,645,740 | 7/1997 | Naiman et al. | 219/121.68 |
| 5,656,186 | 8/1997 | Mourou et al. | 219/121.69 |
| 5,720,894 | 2/1998 | Neev et al. | 216/65 |

FOREIGN PATENT DOCUMENTS

| | | |
|---|---|---|
| 0714641 | 6/1996 | European Pat. Off. . |
| 0815804 | 1/1998 | European Pat. Off. . |
| 0820738 | 1/1998 | European Pat. Off. . |
| 4432938 | 3/1995 | Germany . |
| 8908529 | 9/1989 | WIPO . |
| 9527587 | 10/1995 | WIPO . |

*Primary Examiner*—Patrick Ryan
*Assistant Examiner*—M. Alexandra Elve
*Attorney, Agent, or Firm*—Browdy and Neimark

[57] ABSTRACT

In a method of producing microstructural medical implants by laser material processing, it is provided to make use of a tunable laser beam of a pulse length in the order of magnitude of femtoseconds, and of a laser irradition that is variable in its frequency of pulse repetition, laser capacity and/or velocity of displacement for gentle material treatment without melting to take place.

14 Claims, 2 Drawing Sheets

METHOD OF PRODUCING MICROSTRUCTURAL MEDICAL IMPLANTS

BACKGROUND OF THE INVENTION

1. Field of the Invention

The invention relates to a method of producing microstructural medical implants by laser material processing and in particular by the laser cutting of bioresorbable vessel wall supports.

2. Background Art

As for the background of the invention, numerous implants are known in medical technology, which consist of medical technological materials such as metal alloys or polymers and are structured by cutting processes. Vessel wall supports for use in the human heart are to be mentioned by way of example; they are denoted as "stents" in technical language. So as to avoid unnecessary irritation of the implant contacting tissue, for instance the inside wall of a blood vessel of the heart in the case of an intravascular stent, the edges of the implant structure are to be as smooth and flash-free as possible.

The prior art teaches to manufacture microstructural medical implants by laser cutting processes that originate from conventional material processing technology. Fundamentally, the use of lasers permits the production of microstructures at a high precision and a high working speed.

As a rule, the conventional laser cutting processes mentioned make use of continuous-wave lasers or possibly tunable lasers of pulse lengths in an order of magnitude ranging from nanoseconds to milliseconds. Consequently, the time of action of the laser on the material at the respective spot of machining is so long that in addition to the job of material cutting, considerable heat build-up is produced in the microenvironment of the edge of cut. Minimal quantities of the material are melted, which rigidify irregularly after the time of action of the laser beam or in between the individual pulses of long duration. This causes disadvantageous flashing of the edges of cut.

The flashing mentioned above requires aftertreatment jobs for deflashing. A customary method therefor is electropolishing, which is however very complicated regularly and produces only minor improvements. Further, electropolishing cannot be used because of the low electrical conductivity of many materials, in particular polymers.

So as to avoid the mentioned drawbacks, use may be made of an alternative cutting method such as electrical discharge machining. This is accompanied with an increase in the time consumed for material working as well as a reduction of precision. Owing to the low electrical conductivity of polymers, the use of electrical discharge machining is not possible with these materials.

Finally attention is drawn to the fact that a process for laser material processing is known from WO 95/27586 A, using very short laser pulses in the range of femtoseconds. Various samples such as a gold assay, a sheet of glass and a sample of body tissue (cornea) are exposed to short laser pulses in the range of femtoseconds, microscopical holes and ablation spots being created thereby.

SUMMARY OF THE INVENTION

Proceeding from these problems, it is an object of the invention to specify a method of producing microstructural medical implants by laser material processing, by means of which to produce as flash-free as possible edges of cut without any complicated aftertreatment.

This object is attained by a method wherein the treatment by a tunable laser beam of a pulse length in the range of 10 to 10000 femtoseconds and an adjusted combination of the parameters of frequency of pulse repetition, pulse energy and of velocity of displacement of the workpiece relative to the laser beam is effected for gentle material treatment "without melting" to take place. The term "without melting" means that uncontrolled melting processes no longer occur in the material to be worked, any flashing of edges of machining and in particular of edges of cut being precluded. The parameters of frequency of pulse repetition and/or laser capacity and/or the velocity of displacement of the workpiece relative to the laser beam must be adapted and combined correspondingly. The preclusion of uncontrolled melting processes becomes generally feasible by the laser pulse length being reduced as far as to the range specified, which leads to a decrease in the need of laser pulse energy and reduces the heat build-up so strongly that undesirable and uncontrolled melting processes are suppressed. In the cutting of medical technological materials, this helps avoid the flashing of the edges of cut and any thermal or photochemical impairment of the workpiece material. The latter explanations are to be subsumed under the terms "gentle treatment of material".

As regards the background of the technique, according to the invention, of femtosecond lasering, it can be said in short that so far short pulse lengths of this type have been used to some extent only in data and information technology where high data transfer rates have been attained because of the short pulse lengths. However, this kind of application requires only low laser capacities.

Preferred embodiments of the method according to the invention as well as further features, details and advantages of the invention will become apparent from the ensuing description of an exemplary embodiment of the subject matter of the invention, taken in conjunction with the annexed drawings.

DESCRIPTION OF THE PREFERRED EMBODIMENT

Figure 1:
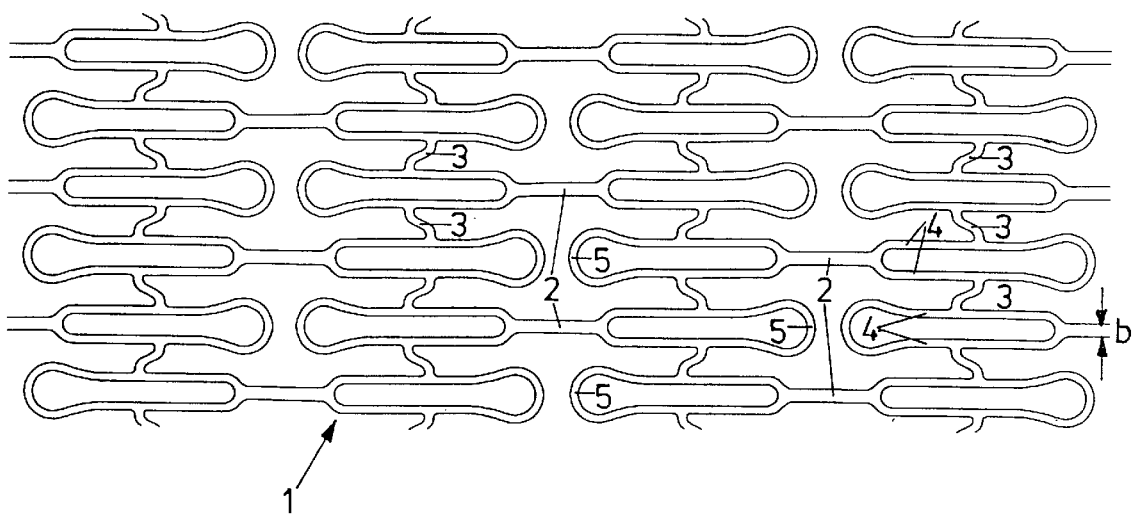
FIG. 1 is a developed view of the structure of a "stent"

As seen in FIG. 1, a "stent" 1 which is known per se consists of a microstructural network of lengthwise ribs 2 and crosswise ribs 3 connecting the latter. The lengthwise ribs 2 branch into parallel strands 4 which are joined by twos at their ends by way of an arc 5. By their branching strands 4, the lengthwise ribs 2 continue to the left and to the right of FIG. 1 as far as to the end of the tubular "stent". In the direction of the crosswise ribs 3, the structure is bent cylindrically so that the crosswise ribs 3 ending at the top of FIG. 1 pass into the crosswise ribs 3 ending at the bottom. As regards the order of magnitude, the widths b of the ribs 2, 3 are in the range of submillimeters.

The "stent" seen in FIG. 1 is bioresorbable. It consists of the material of poly-hydroxybutyrate (PHB).

Figure 2:
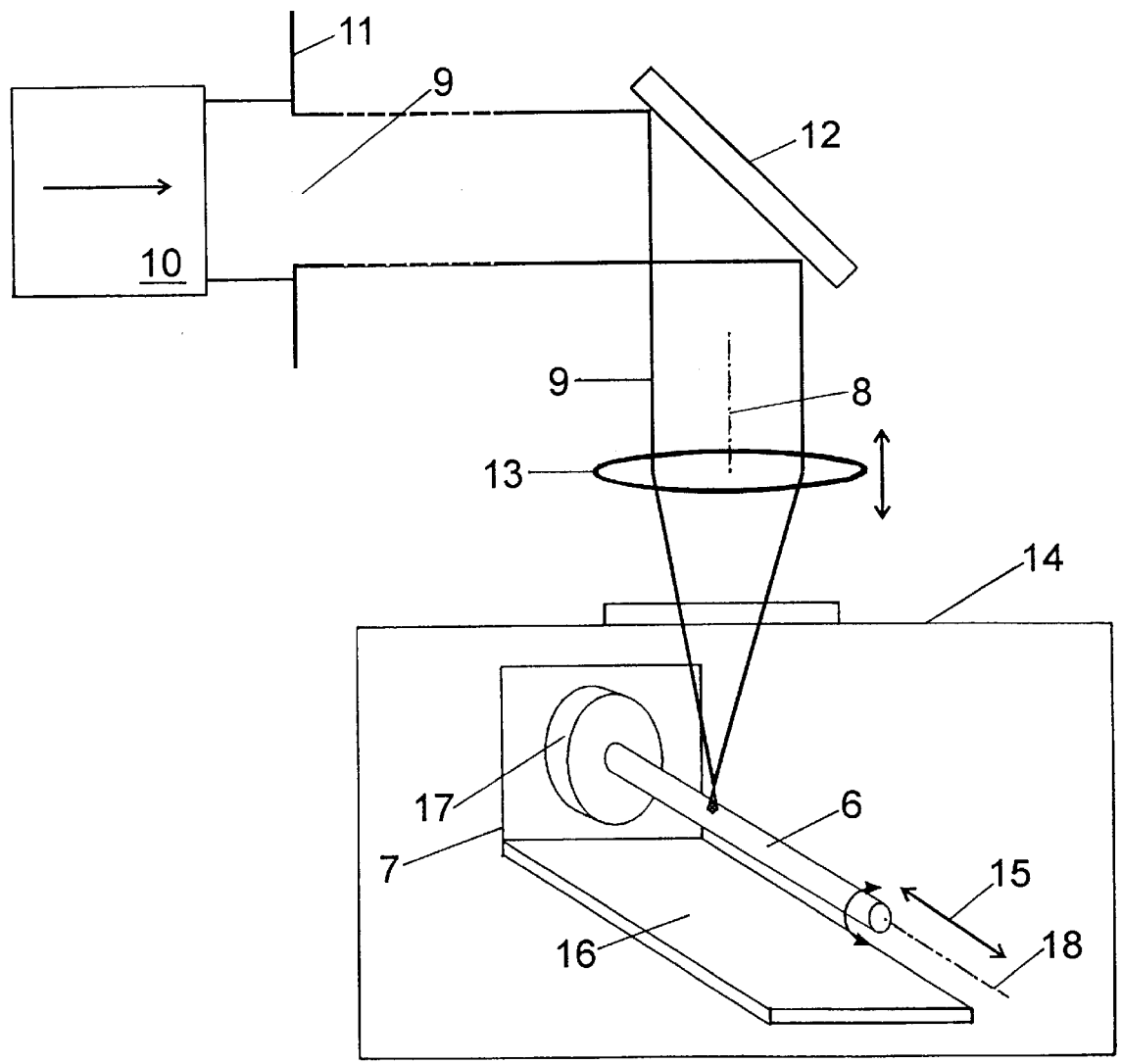
FIG. 2 is a diagrammatic illustration of an apparatus for tunable laser cutting by ultra-short pulse lengths of the "stent" according to FIG. 1.

The apparatus seen in FIG. 2 serves to produce the "stent" 1 with its structure of lengthwise and crosswise ribs 2, 3 as well as strands 4 and arcs 5. A cylindrical PHB stent blank 6 is fixed on a manipulator 7 which provides for a displacement of the blank 6 relative to laser beam 9 which is stationary in its axis 8.

The laser beam 9 is produced by a tunable titanium sapphire laser 10, having a variable wavelength of 760 to 810 mm. The pulse energy is approximately 1 mJ, it may however be selected to be as low as 10 μJ or less. The pulse length is variable, amounting at least to 120 fs. The laser works at a frequency of pulse repetition in the range from 0.1 to 10 kHz at maximum. Corresponding completions of the commercially available titanium sapphire laser have allowed for the laser system to be further adapted to the method according to the invention. For instance a so-called half-wave plate is integrated for energy variation and a rapid mechanical shutter for computer controlled triggering of the laser.

As regards the path of the laser beam 9, FIG. 2 roughly outlines that the laser beam 9 is led through a diaphragm 11 and projected on the "stent" blank 6 by means of the lens 13 with a tilted mirror 12 being interconnected.

The mentioned manipulator 17 is lodged in a vacuum chamber 14. Laser processing takes place at a pressure of less than $10^{-4}$ mbar. Working under a processing gas or in the air is also possible.

The manipulator 7 possesses two axes relative to the workpiece 6, namely a linear axis 15 in the form of a correspondingly adjustable support 16. A turning gear 17 is disposed on the support, having the axis of rotation 18, relative to which the "stent" blank 6 is held concentrically in a chuck (not shown). By means of overlapped motion of the blank 6 along the linear axis 15 and by rotation about the axis of rotation 18 combined with simultaneous exposure of the blank to ultra-short high performance laser pulses, a "stent" of the structure seen in FIG. 1 can be cut from the blank 6 accurately and without flashing on the edges. In doing so, also thermal or photochemical impairment of the PHB material is avoided owing to the conditions of exposure, as a result of which the material properties such as resorbability and mechanical elasticity remain unchanged.

Attention is drawn to the fact that the laser beam, instead of being projected by the diaphragm 11, may also be focused on the workpiece. Another possibility resides in directing the laser beam on to the workpiece by means of a diffractive optic, which is frequently called a "hologram" in technical language. Furthermore, use can be made not only of a stationary axis 8 of the laser beam 9, but the laser beam 9—possibly by the overlapping of workpiece motion—can be passed over the workpiece by means of a laser scanner. The respective mode of working will depend on the structure to be attained an on the material of the workpiece.

What is claimed is:

1. A method of producing a microstructural medical implant by laser cutting of vessel wall supports (1) made of a bioresorbable material, wherein said laser cutting is effected by a tunable laser beam (9) of a pulse length in a range of 10 to 10000 femtosecond and of an adjusted combination of laser parameters comprising frequency of pulse repetition, pulse energy and velocity of displacement of a workpiece (6), constituting the vessel wall support, relative to the laser beam (9), said pulse length and combination of laser parameters being adapted to cut the workpiece (6) without melting of the bioresorbable material to take place.

2. A method according to claim 1, wherein the pulse length ranges from 100 to 1000 femtoseconds.

3. A method according to claim 1, wherein the pulse energy ranges from approximately 10 μJ to 1 mJ.

4. A method according to claim 1, wherein the frequency of pulse repetition ranges from 0.1 to 10 kHz.

5. A method according to claim 1, wherein a titanium sapphire laser of a variable wavelength of 760 to 810 nm is used for the production of the laser beam.

6. A method according to claim 1, wherein the laser beam (9) is led through a diaphragm (11) and projected on the workpiece (6).

7. A method according to claim 1, wherein the laser beam (9) is focused on the workpiece (6).

8. A method according to claim 1, wherein the laser beam (9) is directed on to the workpiece (6) by means of a diffractive optic.

9. A method according to claim 1, wherein the treatment by laser beam takes place in a vacuum (14) or under a processing gas or in the air.

10. A method according to claim 1, wherein a bioresorbable vessel wall support (1), in particular of poly-hydroxybutyrate, is provided with a structure of cross-linked ribs (2, 3) by cutting lasering.

11. A method according to claim 1, wherein the workpiece (6), for being lasered, is passed on a manipulator (7) by displacement relative to the laser beam (9) which is preferably stationary in its axis (8).

12. A method according to claim 1, wherein a laser scanner is used for the laser beam to be passed over the workpiece (6).

13. A method of producing a microstructural medical implant by laser cutting of vessel wall supports (1) made of a bioresorbable marerial, wherein said laser cutting is effected by a tunable laser beam (9) of a pulse length in a range of 100 to 1000 femtoseconds and of an adjusted combination of laser parameters which are frequency of pulse repetition ranging from 0.1 to 10 kHz, pulse energy ranging from 10 mJ to 1 mJ and velocity of displacement of a workpiece (6), constituting the vessel wall support, relative to the laser beam (9), said pulse length and combination of laser parameters are adapted to cut the workpiece (6) without melting of the bioresorbable material.

14. A method of producing a microstructural medical implant by laser cutting of vessel wall supports (1) made of poly-hydroxybutyrate as a bioresorbable material, wherein said laser cutting is effected by a tunable laser beam (9) of a pulse length in a range of 10 to 10000 femtoseconds and of an adjusted combination of laser parameters which are frequency of pulse repetition, pulse energy, and velocity of displacement of a workpiece (6), constituting vessel wall support, relative to the laser beam (9), said pulse length and combination of laser parameters are adapted to cut the workpiece (6) to a vessel wall support (1) of said poly-hydroxybutyrate without melting of said bioresorbable material and providing the vessel wall support with a structure of cross-linked ribs (2, 3).

* * * * *